(12) United States Patent
Terrill et al.

(10) Patent No.: US 9,867,643 B2
(45) Date of Patent: *Jan. 16, 2018

(54) POLYAXIAL LOCKING MECHANISM

(71) Applicant: Zimmer, Inc., Warsaw, IN (US)

(72) Inventors: Lance Nathan Terrill, Oviedo, FL (US); Matthew David Schultz, Orlando, FL (US); Bjorn N. Rindal, Chandler, AZ (US)

(73) Assignee: Zimmer, Inc., Warsaw, IN (US)

( * ) Notice: Subject to any disclaimer, the term of this patent is extended or adjusted under 35 U.S.C. 154(b) by 39 days.

This patent is subject to a terminal disclaimer.

(21) Appl. No.: 15/342,206

(22) Filed: Nov. 3, 2016

(65) Prior Publication Data

US 2017/0042595 A1 Feb. 16, 2017

Related U.S. Application Data

(63) Continuation of application No. 14/025,267, filed on Sep. 12, 2013, now Pat. No. 9,510,880.

(Continued)

(51) Int. Cl.
*A61B 17/80* (2006.01)
*A61B 17/86* (2006.01)

(52) U.S. Cl.
CPC ...... *A61B 17/8057* (2013.01); *A61B 17/8052* (2013.01); *A61B 17/8605* (2013.01); *A61B 17/80* (2013.01)

(58) Field of Classification Search
CPC . A61B 17/80; A61B 17/8004; A61B 17/8009; A61B 17/8014; A61B 17/8019;
(Continued)

(56) References Cited

U.S. PATENT DOCUMENTS 5,147,361 A 9/1992 Ojima et al.
5,275,601 A * 1/1994 Gogolewski ....... A61B 17/8052
411/399

(Continued)

FOREIGN PATENT DOCUMENTS

CN 105555213 A 5/2016
DE 4343117 A1 6/1995
(Continued)

OTHER PUBLICATIONS

"U.S. Appl. No. 14/025,267, Advisory Action mailed Jun. 30, 2015", 3 pgs.

(Continued)

*Primary Examiner* — Eric S Gibson
(74) *Attorney, Agent, or Firm* — Schwegman Lundberg & Woessner, P.A.

(57) ABSTRACT

A bone plate system comprises a bone plate including a first surface and a second surface, the bone plate including at least one threaded aperture, the threaded aperture being tapered between the first surface and the second surface. The bone plate system further comprises at least one fastener including an elongate shaft and a threaded head, the threaded head being tapered between a proximal end of the threaded head and a distal end of the threaded head, wherein a plurality of circumferentially spaced recesses are formed in the threaded head and define a plurality of threaded tabs. The at least one fastener is configured for insertion within the at least one threaded aperture at a plurality of different insertion angles while achieving a locking engagement between the threaded head and the threaded aperture.

20 Claims, 10 Drawing Sheets

Related U.S. Application Data

(60) Provisional application No. 61/865,247, filed on Aug. 13, 2013.

(58) Field of Classification Search
CPC .......... A61B 17/8023; A61B 17/8028; A61B 17/8052; A61B 17/8057
USPC .................................... 606/70, 71, 280–299
See application file for complete search history.

(56) References Cited

U.S. PATENT DOCUMENTS

| | | | |
|---|---|---|---|
| 5,520,690 | A | 5/1996 | Errico et al. |
| 5,531,746 | A | 7/1996 | Errico et al. |
| 5,607,426 | A | 3/1997 | Ralph et al. |
| 5,607,428 | A | 3/1997 | Lin |
| 5,643,265 | A | 7/1997 | Errico et al. |
| 5,647,873 | A | 7/1997 | Errico et al. |
| 5,669,911 | A | 9/1997 | Errico et al. |
| 5,690,630 | A | 11/1997 | Errico et al. |
| 5,709,686 | A | 1/1998 | Talos et al. |
| 5,725,588 | A | 3/1998 | Errico et al. |
| 5,735,853 | A | 4/1998 | Olerud |
| 5,741,258 | A | 4/1998 | Klaue et al. |
| 5,785,712 | A | 7/1998 | Runciman et al. |
| 5,807,396 | A | 9/1998 | Raveh |
| 5,810,823 | A | 9/1998 | Klaue et al. |
| 5,817,094 | A | 10/1998 | Errico et al. |
| 5,876,402 | A | 3/1999 | Errico et al. |
| 5,882,350 | A | 3/1999 | Ralph et al. |
| 5,931,838 | A | 8/1999 | Vito |
| 5,951,558 | A | 9/1999 | Fiz |
| 5,954,722 | A | 9/1999 | Bono |
| 6,030,389 | A | 2/2000 | Wagner et al. |
| 6,129,730 | A * | 10/2000 | Bono ................ A61B 17/8047 606/271 |
| 6,139,550 | A | 10/2000 | Michelson |
| 6,152,927 | A | 11/2000 | Farris et al. |
| 6,193,721 | B1 | 2/2001 | Michelson |
| 6,206,881 | B1 * | 3/2001 | Frigg ................ A61B 17/8052 606/291 |
| 6,273,889 | B1 | 8/2001 | Richelsoph |
| 6,306,139 | B1 | 10/2001 | Fuentes |
| 6,306,140 | B1 * | 10/2001 | Siddiqui ............. A61B 17/863 606/315 |
| 6,322,562 | B1 | 11/2001 | Wolter |
| 6,358,250 | B1 | 3/2002 | Orbay |
| RE37,665 | E | 4/2002 | Ralph et al. |
| 6,364,882 | B1 | 4/2002 | Orbay |
| 6,383,186 | B1 | 5/2002 | Michelson |
| 6,398,783 | B1 | 6/2002 | Michelson |
| 6,440,135 | B2 | 8/2002 | Orbay et al. |
| 6,454,769 | B2 | 9/2002 | Wagner et al. |
| 6,454,771 | B1 | 9/2002 | Michelson |
| 6,508,819 | B1 | 1/2003 | Orbay |
| 6,527,776 | B1 | 3/2003 | Michelson |
| 6,558,387 | B2 | 5/2003 | Errico et al. |
| 6,575,975 | B2 | 6/2003 | Brace et al. |
| 6,592,586 | B1 | 7/2003 | Michelson |
| 6,669,700 | B1 | 12/2003 | Farris et al. |
| 6,689,133 | B2 | 2/2004 | Morrison et al. |
| 6,706,046 | B2 | 3/2004 | Orbay et al. |
| 6,712,820 | B2 | 3/2004 | Orbay |
| 6,730,090 | B2 | 5/2004 | Orbay et al. |
| 6,730,091 | B1 | 5/2004 | Pfefferle et al. |
| 6,730,127 | B2 | 5/2004 | Michelson |
| 6,755,832 | B2 | 6/2004 | Happonen et al. |
| 6,767,351 | B2 | 7/2004 | Orbay et al. |
| 6,786,909 | B1 * | 9/2004 | Dransfeld .......... A61B 17/8052 606/280 |
| 6,793,658 | B2 | 9/2004 | LeHuec et al. |
| 6,866,665 | B2 | 3/2005 | Orbay |
| 6,890,334 | B2 | 5/2005 | Brace et al. |
| 6,893,444 | B2 | 5/2005 | Orbay |
| 6,916,320 | B2 | 7/2005 | Michelson |
| 6,926,718 | B1 | 8/2005 | Michelson |
| 6,936,050 | B2 | 8/2005 | Michelson |
| 6,955,677 | B2 | 10/2005 | Dahners |
| 6,974,461 | B1 | 12/2005 | Wolter |
| 7,001,387 | B2 | 2/2006 | Farris et al. |
| 7,001,388 | B2 | 2/2006 | Orbay et al. |
| RE39,089 | E | 5/2006 | Ralph et al. |
| 7,041,105 | B2 | 5/2006 | Michelson |
| 7,077,844 | B2 | 7/2006 | Michelson |
| 7,087,057 | B2 | 8/2006 | Konieczynski et al. |
| 7,115,130 | B2 | 10/2006 | Michelson |
| 7,137,984 | B2 | 11/2006 | Michelson |
| 7,137,987 | B2 | 11/2006 | Patterson et al. |
| 7,175,623 | B2 | 2/2007 | Thramann et al. |
| 7,175,624 | B2 | 2/2007 | Konieczynski et al. |
| 7,179,260 | B2 * | 2/2007 | Gerlach ............ A61B 17/8014 606/291 |
| 7,189,237 | B2 | 3/2007 | Huebner |
| 7,195,633 | B2 | 3/2007 | Medoff et al. |
| 7,220,263 | B2 | 5/2007 | Cordaro |
| 7,229,442 | B2 | 6/2007 | Schafer |
| 7,229,443 | B2 | 6/2007 | Eberlein et al. |
| 7,250,053 | B2 | 7/2007 | Orbay |
| 7,250,054 | B2 | 7/2007 | Allen et al. |
| 7,255,701 | B2 | 8/2007 | Allen et al. |
| 7,273,481 | B2 | 9/2007 | Lombardo et al. |
| 7,282,053 | B2 | 10/2007 | Orbay |
| 7,294,130 | B2 | 11/2007 | Orbay |
| 7,306,602 | B2 | 12/2007 | Bono et al. |
| 7,309,340 | B2 | 12/2007 | Fallin et al. |
| 7,311,712 | B2 | 12/2007 | Dalton |
| 7,410,496 | B2 | 8/2008 | Derouet |
| 7,425,213 | B2 | 9/2008 | Orbay |
| 7,465,320 | B1 | 12/2008 | Kito et al. |
| 7,524,325 | B2 | 4/2009 | Khalili |
| 7,527,639 | B2 | 5/2009 | Orbay et al. |
| 7,556,831 | B2 | 7/2009 | Quart et al. |
| 7,563,263 | B2 | 7/2009 | Orbay et al. |
| 7,621,957 | B2 | 11/2009 | Errico et al. |
| 7,635,381 | B2 | 12/2009 | Orbay |
| 7,637,928 | B2 | 12/2009 | Fernandez |
| 7,651,497 | B2 | 1/2010 | Michelson |
| 7,655,029 | B2 | 2/2010 | Niederberger et al. |
| 7,682,379 | B2 | 3/2010 | Mathieu et al. |
| 7,686,837 | B2 | 3/2010 | Gasser et al. |
| 7,691,133 | B2 | 4/2010 | Partin |
| 7,695,472 | B2 | 4/2010 | Young |
| 7,695,502 | B2 | 4/2010 | Orbay et al. |
| 7,699,880 | B2 | 4/2010 | Orbay et al. |
| 7,704,255 | B2 | 4/2010 | Michelson |
| 7,717,945 | B2 | 5/2010 | Jensen et al. |
| 7,727,264 | B2 | 6/2010 | Orbay et al. |
| 7,727,266 | B2 | 6/2010 | Lindemann et al. |
| 7,744,638 | B2 | 6/2010 | Orbay |
| 7,749,257 | B2 | 7/2010 | Medoff |
| 7,758,616 | B2 | 7/2010 | LeHuec et al. |
| 7,766,947 | B2 | 8/2010 | Hawkes et al. |
| 7,766,948 | B1 | 8/2010 | Leung |
| 7,771,458 | B2 | 8/2010 | Biedermann et al. |
| 7,776,076 | B2 | 8/2010 | Grady |
| 7,780,664 | B2 | 8/2010 | Orbay |
| 7,780,710 | B2 | 8/2010 | Orbay et al. |
| 7,780,711 | B2 | 8/2010 | Orbay et al. |
| 7,785,327 | B1 | 8/2010 | Navarro et al. |
| 7,794,482 | B2 | 9/2010 | Mathieu et al. |
| 7,857,838 | B2 | 12/2010 | Orbay |
| 7,857,839 | B2 | 12/2010 | Duong et al. |
| 7,875,062 | B2 | 1/2011 | Lindemann et al. |
| 7,896,886 | B2 | 3/2011 | Orbay et al. |
| 7,905,909 | B2 | 3/2011 | Orbay et al. |
| 7,905,910 | B2 | 3/2011 | Gerlach et al. |
| 7,909,858 | B2 | 3/2011 | Gerlach et al. |
| 7,909,860 | B2 | 3/2011 | Rathbun et al. |
| 7,927,341 | B2 | 4/2011 | Orbay et al. |
| 7,931,681 | B2 | 4/2011 | Carls et al. |
| 7,935,137 | B2 | 5/2011 | Gorhan et al. |
| 7,938,850 | B2 | 5/2011 | Orbay et al. |
| 7,942,913 | B2 | 5/2011 | Ziolo et al. |
| 7,951,176 | B2 | 5/2011 | Grady, Jr. et al. |

(56) References Cited

U.S. PATENT DOCUMENTS

| | | | |
|---|---|---|---|
| 7,951,178 B2 | 5/2011 | Jensen | |
| 7,955,364 B2 | 6/2011 | Ziolo et al. | |
| 7,963,981 B2 | 6/2011 | Binder et al. | |
| 7,963,982 B2 | 6/2011 | Kirschman | |
| RE42,545 E | 7/2011 | Ralph et al. | |
| 7,976,570 B2 | 7/2011 | Wagner et al. | |
| 7,981,142 B2 | 7/2011 | Konieczynski et al. | |
| 8,007,523 B2 | 8/2011 | Wagner et al. | |
| 8,075,561 B2* | 12/2011 | Wolter | A61B 17/686 606/71 |
| 8,075,602 B2 | 12/2011 | Lombardo et al. | |
| 8,105,367 B2 | 1/2012 | Austin et al. | |
| 8,114,140 B2 | 2/2012 | Derouet | |
| 8,118,848 B2 | 2/2012 | Ducharme et al. | |
| 8,216,283 B2 | 7/2012 | Mathieu et al. | |
| 8,226,692 B2 | 7/2012 | Mathieu et al. | |
| 8,236,034 B2 | 8/2012 | Binder et al. | |
| 8,246,661 B2 | 8/2012 | Beutter et al. | |
| 8,323,321 B2 | 12/2012 | Gradl | |
| 8,337,535 B2 | 12/2012 | White et al. | |
| 8,343,196 B2 | 1/2013 | Schneider | |
| 8,361,127 B2 | 1/2013 | Biedermann et al. | |
| 8,382,807 B2 | 2/2013 | Austin et al. | |
| 8,382,845 B2 | 2/2013 | Metzger et al. | |
| 8,394,132 B2 | 3/2013 | Lewis et al. | |
| 8,403,967 B2 | 3/2013 | Orbay | |
| 8,439,957 B2 | 5/2013 | Lombardo et al. | |
| 8,460,344 B2 | 6/2013 | Niederberger et al. | |
| 8,460,348 B2 | 6/2013 | Gorhan et al. | |
| 8,480,716 B2 | 7/2013 | Perrow et al. | |
| 8,486,116 B2 | 7/2013 | Heilman | |
| 8,486,118 B2 | 7/2013 | Mathieu et al. | |
| 8,574,268 B2 | 11/2013 | Chan et al. | |
| 8,906,076 B2* | 12/2014 | Mocanu | A61B 17/8057 606/291 |
| 9,510,880 B2 | 12/2016 | Terrill et al. | |
| 2002/0045901 A1 | 4/2002 | Wagner et al. | |
| 2002/0058940 A1* | 5/2002 | Frigg | A61B 17/80 606/291 |
| 2004/0073218 A1* | 4/2004 | Dahners | A61B 17/8057 606/287 |
| 2005/0010226 A1* | 1/2005 | Grady, Jr. | A61B 17/746 606/281 |
| 2005/0049594 A1* | 3/2005 | Wack | A61B 17/1728 606/86 B |
| 2005/0059971 A1 | 3/2005 | Michelson | |
| 2005/0165400 A1* | 7/2005 | Fernandez | A61B 17/8057 606/281 |
| 2005/0187552 A1 | 8/2005 | Michelson | |
| 2005/0261688 A1* | 11/2005 | Grady, Jr. | A61B 17/8057 606/286 |
| 2005/0277937 A1* | 12/2005 | Leung | A61B 17/8057 606/287 |
| 2006/0004361 A1* | 1/2006 | Hayeck | A61B 17/74 606/282 |
| 2006/0009771 A1* | 1/2006 | Orbay | A61B 17/8057 606/291 |
| 2006/0058797 A1 | 3/2006 | Mathieu et al. | |
| 2006/0149256 A1 | 7/2006 | Wagner et al. | |
| 2006/0235400 A1* | 10/2006 | Schneider | A61B 17/8052 606/287 |
| 2007/0043366 A1 | 2/2007 | Pfefferle et al. | |
| 2007/0083207 A1* | 4/2007 | Ziolo | A61B 17/8057 606/287 |
| 2007/0088360 A1* | 4/2007 | Orbay | A61B 17/8057 606/287 |
| 2008/0058817 A1 | 3/2008 | Eberlein et al. | |
| 2008/0119894 A1* | 5/2008 | Ehrhardt | A61B 17/8057 606/280 |
| 2008/0140130 A1* | 6/2008 | Chan | A61B 17/1728 606/280 |
| 2008/0161860 A1 | 7/2008 | Ahrens et al. | |
| 2008/0177330 A1 | 7/2008 | Ralph et al. | |
| 2008/0208259 A1* | 8/2008 | Gilbert | A61B 17/8057 606/280 |
| 2008/0234677 A1* | 9/2008 | Dahners | A61B 17/8047 606/60 |
| 2008/0234749 A1* | 9/2008 | Forstein | A61B 17/8057 606/291 |
| 2008/0234751 A1 | 9/2008 | Mcclintock | |
| 2008/0234752 A1* | 9/2008 | Dahners | A61B 17/8047 606/291 |
| 2008/0243192 A1 | 10/2008 | Jacene et al. | |
| 2008/0288001 A1 | 11/2008 | Cawley et al. | |
| 2008/0300637 A1 | 12/2008 | Austin et al. | |
| 2008/0306550 A1 | 12/2008 | Matityahu | |
| 2009/0018588 A1* | 1/2009 | Eckhof | A61B 17/8057 606/280 |
| 2009/0076553 A1 | 3/2009 | Wolter | |
| 2009/0088807 A1 | 4/2009 | Castaneda et al. | |
| 2009/0143824 A1 | 6/2009 | Austin et al. | |
| 2009/0157121 A1 | 6/2009 | Harris et al. | |
| 2009/0182383 A1 | 7/2009 | Prybyla et al. | |
| 2009/0216282 A1 | 8/2009 | Blake et al. | |
| 2009/0228047 A1 | 9/2009 | Derouet et al. | |
| 2009/0270926 A1 | 10/2009 | Hawkes | |
| 2009/0287257 A1 | 11/2009 | Hagen | |
| 2009/0312803 A1* | 12/2009 | Austin | A61B 17/8014 606/305 |
| 2009/0318978 A1 | 12/2009 | Podgorski et al. | |
| 2010/0042161 A1 | 2/2010 | Worcel | |
| 2010/0057138 A1 | 3/2010 | Murner et al. | |
| 2010/0069969 A1 | 3/2010 | Ampuero et al. | |
| 2010/0076496 A1 | 3/2010 | Fernandez | |
| 2010/0100134 A1* | 4/2010 | Mocanu | A61B 17/863 606/281 |
| 2010/0160973 A1 | 6/2010 | Leung | |
| 2010/0174324 A1 | 7/2010 | Derouet | |
| 2010/0179599 A1 | 7/2010 | Derouet et al. | |
| 2010/0211118 A1 | 8/2010 | Christen et al. | |
| 2010/0222780 A1 | 9/2010 | Lindemann et al. | |
| 2010/0234899 A1 | 9/2010 | Johnson et al. | |
| 2010/0241173 A1 | 9/2010 | Orbay | |
| 2010/0256686 A1 | 10/2010 | Fisher et al. | |
| 2010/0274247 A1 | 10/2010 | Grady, Jr. et al. | |
| 2010/0274296 A1 | 10/2010 | Appenzeller et al. | |
| 2010/0312285 A1* | 12/2010 | White | A61B 17/8605 606/289 |
| 2010/0312286 A1* | 12/2010 | Dell'Oca | A61B 17/8057 606/291 |
| 2010/0324604 A1 | 12/2010 | Mathieu et al. | |
| 2011/0009909 A1* | 1/2011 | Derouet | A61B 17/8057 606/305 |
| 2011/0015682 A1 | 1/2011 | Lewis et al. | |
| 2011/0029024 A1 | 2/2011 | Crainich | |
| 2011/0071572 A1* | 3/2011 | Sixto | A61B 17/8014 606/286 |
| 2011/0082506 A1 | 4/2011 | Lore et al. | |
| 2011/0144700 A1 | 6/2011 | Konieczynski et al. | |
| 2011/0152944 A1 | 6/2011 | Campbell et al. | |
| 2011/0166571 A1 | 7/2011 | Orbay | |
| 2011/0202093 A1 | 8/2011 | Grady, Jr. et al. | |
| 2011/0224671 A1 | 9/2011 | Koay et al. | |
| 2011/0270326 A1 | 11/2011 | Black et al. | |
| 2011/0282393 A1 | 11/2011 | Gerlach et al. | |
| 2011/0301608 A1* | 12/2011 | Roth | A61B 17/8052 606/70 |
| 2011/0319943 A1 | 12/2011 | Donahoe et al. | |
| 2012/0029579 A1 | 2/2012 | Bottlang et al. | |
| 2012/0083847 A1* | 4/2012 | Huebner | A61B 17/8057 606/281 |
| 2012/0109216 A1 | 5/2012 | Austin et al. | |
| 2012/0136396 A1 | 5/2012 | Baker et al. | |
| 2012/0143193 A1 | 6/2012 | Hulliger | |
| 2012/0197308 A1 | 8/2012 | Gonzalez-Hernandez | |
| 2012/0259371 A1 | 10/2012 | Mathieu et al. | |
| 2012/0265255 A1* | 10/2012 | Hilse | A61B 17/8014 606/290 |
| 2013/0096631 A1* | 4/2013 | Leung | A61B 17/8605 606/286 |
| 2013/0116735 A1 | 5/2013 | Schneider | |

(56) References Cited

U.S. PATENT DOCUMENTS

| | | | |
|---|---|---|---|
| 2013/0158608 A1* | 6/2013 | Viola | A61B 17/80 606/289 |
| 2013/0172943 A1 | 7/2013 | Austin et al. | |
| 2013/0184749 A1 | 7/2013 | Lore et al. | |
| 2013/0184765 A1* | 7/2013 | Beyar | A61B 17/8052 606/281 |
| 2013/0190828 A1 | 7/2013 | Schneider | |
| 2014/0005728 A1* | 1/2014 | Koay | A61B 17/8057 606/281 |
| 2014/0039563 A1* | 2/2014 | Mocanu | A61B 17/8057 606/291 |
| 2014/0236245 A1* | 8/2014 | Hainard | A61B 17/8605 606/291 |
| 2015/0051651 A1* | 2/2015 | Terrill | A61B 17/8057 606/289 |

FOREIGN PATENT DOCUMENTS

| | | |
|---|---|---|
| DE | 10309090 A1 | 9/2004 |
| DE | 20321244 A1 | 6/2006 |
| DE | 20321245 U1 | 6/2006 |
| DE | 102005015496 A1 | 11/2006 |
| DE | 20321551 U1 | 12/2007 |
| DE | 20321552 U1 | 12/2007 |
| EP | 1531745 | 5/2005 |
| EP | 1633260 | 3/2006 |
| EP | 1767160 A2 | 3/2007 |
| EP | 1996096 | 12/2008 |
| EP | 1996120 | 12/2008 |
| EP | 1567072 | 9/2009 |
| EP | 2139414 | 1/2010 |
| EP | 2182870 | 5/2010 |
| EP | 1741397 B1 | 7/2010 |
| EP | 2207491 | 7/2010 |
| EP | 2248479 A1 | 11/2010 |
| EP | 2258288 A1 | 12/2010 |
| EP | 2339969 | 7/2011 |
| EP | 1731107 B1 | 2/2012 |
| EP | 2421457 | 2/2012 |
| EP | 2429434 | 3/2012 |
| EP | 2559392 A1 | 2/2013 |
| EP | 2559393 A1 | 2/2013 |
| EP | 2559394 A1 | 2/2013 |
| EP | 2575655 | 4/2013 |
| EP | 2595554 | 5/2013 |
| JP | 2016529998 A | 9/2016 |
| WO | WO-2008055648 A2 | 5/2008 |
| WO | WO-2008115318 A1 | 9/2008 |
| WO | WO-2011041624 A2 | 4/2011 |
| WO | WO 2013053539 A1 | 4/2013 |
| WO | WO-2013059090 A1 | 4/2013 |
| WO | WO-2015023663 A2 | 2/2015 |

OTHER PUBLICATIONS

"U.S. Appl. No. 14/025,267, Final Office Action mailed Apr. 6, 2015", 16 pgs.
"U.S. Appl. No. 14/025,267, Final Office Action mailed Apr. 14, 2016", 14 pgs.
"U.S. Appl. No. 14/025,267, Non Final Office Action mailed Sep. 28, 2015", 13 pgs.
"U.S. Appl. No. 14/025,267, Non Final Office Action mailed Dec. 23, 2014", 16 pgs.
"U.S. Appl. No. 14/025,267, Notice of Allowance mailed Aug. 3, 2016", 8 pgs.
"U.S. Appl. No. 14/025,267, Response filed Mar. 23, 2015 to Non-Final Office Action mailed Dec. 23, 2014", 14 pgs.
"U.S. Appl. No. 14/025,267, Response filed Mar. 28, 2016 to Non Final Office Action mailed Sep. 28, 2015", 17 pgs.
"U.S. Appl. No. 14/025,267, Response filed Jun. 8, 2015 to Final Office Action mailed Apr. 6, 2015", 14 pgs.
"U.S. Appl. No. 14/025,267, Response filed Jul. 14, 2016 to Final Office Action mailed Apr. 14, 2016", 13 pgs.
"U.S. Appl. No. 14/025,267, Response to Advisory Action mailed Jun. 30, 2015", 18 pgs.
"International Application Serial No. PCT/US2014/050712, International Preliminary Report on Patentability mailed Feb. 25, 2016", 7 pgs.
"International Application Serial No. PCT/US2014/050712, International Search Report mailed Feb. 6, 2015", 3 pgs.
"International Application Serial No. PCT/US2014/050712, Written Opinion mailed Feb. 6, 2015", 5 pgs.

* cited by examiner

POLYAXIAL LOCKING MECHANISM

This application is a continuation of U.S. patent application Ser. No. 14/025,267, entitled "POLYAXIAL LOCKING MECHANISM", and filed on Sep. 12, 2013, which claims the benefit of U.S. Provisional Patent Application Ser. No. 61/865,247, entitled "POLYAXIAL LOCKING MECHANISM", and filed on Aug. 13, 2013, the benefit of priority of each of which are claimed hereby, and are incorporated by reference herein in its entirety.

BACKGROUND

The present patent application relates to locking mechanisms, and, more particularly, to polyaxial locking mechanisms for surgical components such as bone plates.

In certain orthopedic surgical procedures, it is necessary to secure multiple bones or bone portions relative to each other. For example, in wrist or ankle surgeries, the joining of two or more bone portions or fragments may be required to promote healing and restore function. The need for such procedures may be the result of physical trauma from fractures or dislocations, degenerative diseases, or the like.

Various types of bone plate systems can be used for internal fixation of bones. Exemplary bone plate systems can include a bone plate that is configured to be attached to one or more bone portions spanning a fracture line. The bone plate generally includes a plurality of apertures through which bone screws and/or bone pegs are inserted for engaging the bone. In an example, the bone plate systems can include locking screws, which can be adapted for locking in corresponding plate apertures in a fixed orientation. An advantage of "locked plating" systems is that they do not require the bone plate to be compressed to the bone. Rather, the interface formed between the bone plate and the locking screws can eliminate the need for compression between the plate and the bone. In another example, the bone plate systems can include non-locking screws, which can be configured for insertion at an orientation selected by the user. Unlike "locked plating" systems, "non-locked plating" systems rely on the friction formed between the bone plate and the bone when the screw is inserted through the bone plate and tightened.

Although numerous bone plate systems exist for use in orthopedic surgical procedures, there is still a need for improved bone plate systems that provide the locking characteristics associated with traditional locking screws as well as the variable screw orientation associated with traditional non-locking screws.

OVERVIEW

To better illustrate the cleaning system disclosed herein, a non-limiting list of examples is provided here:

In Example 1, a bone plate system can be provided that includes a bone plate having a first surface and a second surface, the bone plate including at least one threaded aperture, the threaded aperture being tapered between the first surface and the second surface. The bone plate system further includes at least one fastener including an elongate shaft and a threaded head, the threaded head being tapered between a proximal end of the threaded head and a distal end of the threaded head, wherein a plurality of circumferentially spaced recesses are formed in the threaded head and define a plurality of threaded tabs. The at least one fastener is configured for insertion within the at least one threaded aperture at a plurality of different insertion angles while achieving a locking engagement between the threaded head and the threaded aperture.

In Example 2, the bone plate system of Example 1 is optionally configured such that a first taper angle is formed between a longitudinal axis of the threaded aperture and an internally threaded surface of the threaded aperture, and a second taper angle is formed between a longitudinal axis of the threaded head and an externally threaded surface of the threaded head, wherein the first taper angle is greater than the second taper angle.

In Example 3, the bone plate system of Example 2 is optionally configured such that the first taper angle is between about 10 degrees and about 20 degrees, and the second taper angle is between about 5 degrees and about 15 degrees.

In Example 4, the bone plate system of any one of or any combination of Examples 2-3 is configured such that the plurality of recesses extend from the proximal end to the distal end of the threaded head in a direction that is substantially parallel to the longitudinal axis of the threaded head.

In Example 5, the bone plate system of any one of or any combination of Examples 2-4 is optionally configured such that the internally threaded surface of the threaded aperture includes double lead threads.

In Example 6, the bone plate system of any one of or any combination of Examples 1-5 is optionally configured such that the threaded aperture includes internal threads defining a first pitch, and the threaded head includes external threads defining a second pitch.

In Example 7, the bone plate system of Example 6 is optionally configured such that the first pitch and the second pitch are the same.

In Example 8, the bone plate system of Example 6 is optionally configured such that the first pitch and the second pitch are different.

In Example 9, the bone plate system of any one of or any combination of Examples 1-8 is optionally configured to include three or more recesses in the threaded head.

In Example 10, the bone plate system of any one of or any combination of Examples 1-9 is optionally configured such that a circumference of the threaded head includes a threaded circumference portion defined by the threaded tabs and a non-threaded circumference portion defined by the recesses, wherein the threaded circumference portion is greater than the non-threaded circumference portion.

In Example 11, the bone plate system of any one of or any combination of Examples 1-10 is optionally configured such that the threaded head is at least partially formed from a first material that is softer than a second material of the bone plate such that the threaded head can deform during insertion within the threaded aperture of the bone plate.

In Example 12, a bone plate system can be provided that includes a bone plate including at least one tapered aperture having a longitudinal axis and a threaded internal surface, the tapered aperture defining a first taper angle between the longitudinal axis of the tapered aperture and the threaded internal surface. The bone plate system further includes at least one fastener including an elongate shaft and a tapered head having a threaded external surface and a longitudinal axis, the tapered head defining a second taper angle between the longitudinal axis of the tapered head and the threaded external surface, wherein a plurality of circumferentially spaced recesses are formed in the tapered head and define interruptions in the threaded external surface of the tapered head. The first taper angle of the tapered aperture is greater than the second taper angle of the tapered head such that the at least one fastener can be inserted within the at least one tapered aperture at a plurality of different insertion angles.

In Example 13, the bone plate system of Example 12 is optionally configured such that the first taper angle is between about 10 degrees and about 20 degrees, and the second taper angle is between about 5 degrees and about 15 degrees.

In Example 14, the bone plate system of any one of or any combination of Examples 12-13 is optionally configured such that the interruptions in the threaded external surface of the tapered head define a plurality of threaded tabs on the tapered head.

In Example 15, the bone plate system of Example 14 is optionally configured such that a circumferential surface area defined by the threaded tabs is greater than a circumferential surface area defined by the recesses in the tapered head.

In Example 16, the bone plate system of any one of or any combination of Examples 12-15 is optionally configured such that the threaded internal surface of the tapered aperture includes threads defining a first pitch and the threaded external surface of the tapered head includes threads defining a second pitch, wherein the first pitch and the second pitch are the same.

In Example 17, the bone plate system of any one of or any combination of Examples 12-15 is optionally configured such that the threaded internal surface of the tapered aperture includes threads defining a first pitch and the threaded external surface of the tapered head includes threads defining a second pitch, wherein the first pitch and the second pitch are different.

In Example 18, a polyaxial locking mechanism can be provided that includes at least one tapered aperture formed in a component, wherein the tapered aperture includes an internally threaded surface. The polyaxial locking mechanism further includes at least one fastener configured for insertion within the at least one tapered aperture at a plurality of different insertion angles, the at least one fastener including an elongate shaft and a tapered head, wherein a plurality of circumferentially spaced recesses are formed in the tapered head and define a plurality of threaded tabs. The tapered head includes a threaded surface area portion defined by the threaded tabs and a non-threaded surface area portion defined by the recesses, wherein the threaded surface area portion is greater than the non-threaded surface area portion.

In Example 19, the polyaxial locking mechanism of Example 18 is optionally configured such that the internally threaded surface of the tapered aperture includes double lead threads.

In Example 20, the polyaxial locking mechanism of any one of or any combination of Examples 18-19 is optionally configured such that the tapered head is at least partially formed from a first material that is softer than a second material of the component such that the tapered head can deform dining insertion within the tapered aperture of the component.

In Example 21, the bone plate system or polyaxial locking mechanism of any one of or any combination of Examples 1-20 is optionally configured such that all elements or options recited are available to use or select from.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present patent application generally relates to bone plate systems having a polyaxial locking relationship between at least one fastener and at least one aperture in a bone plate. The bone plate system can include any type of bone plate configured for attachment to one or more bones, bone portions, or bone fragments, such as bones of a patient's extremities. In certain examples, the bone plate can be configured for attachment to a hand, a wrist, a foot, an ankle, or a spine. The at least one fastener of the bone plate system can be configured for insertion in the at least one aperture in a plurality of different insertion angles defining a plurality of different axes, i.e., the at least one fastener can be "polyaxial." An externally threaded head surface of the at least one fastener can be configured to engage an internally threaded aperture surface of the at least one aperture to provide a locking engagement between the at least one fastener and the bone plate. An advantage of such "locked plating" systems can be that they do not require the bone plate to be compressed to the bone upon implantation due to the interface formed between the bone plate and the head of the fastener.

For purposes of example only, the bone plate system of the present disclosure is described with reference to a fastener in the form of a bone screw having a threaded head and a threaded shaft. However, numerous other types of fasteners can be used in place of or in addition to a bone screw, such as a bone peg having a threaded head and a non-threaded shaft. Thus, bone screws are described merely for purposes of example and not limitation, and the scope of the present disclosure covers any fastener that allows for polyaxial insertion and locking engagement with a bone plate.

Figure 1A:
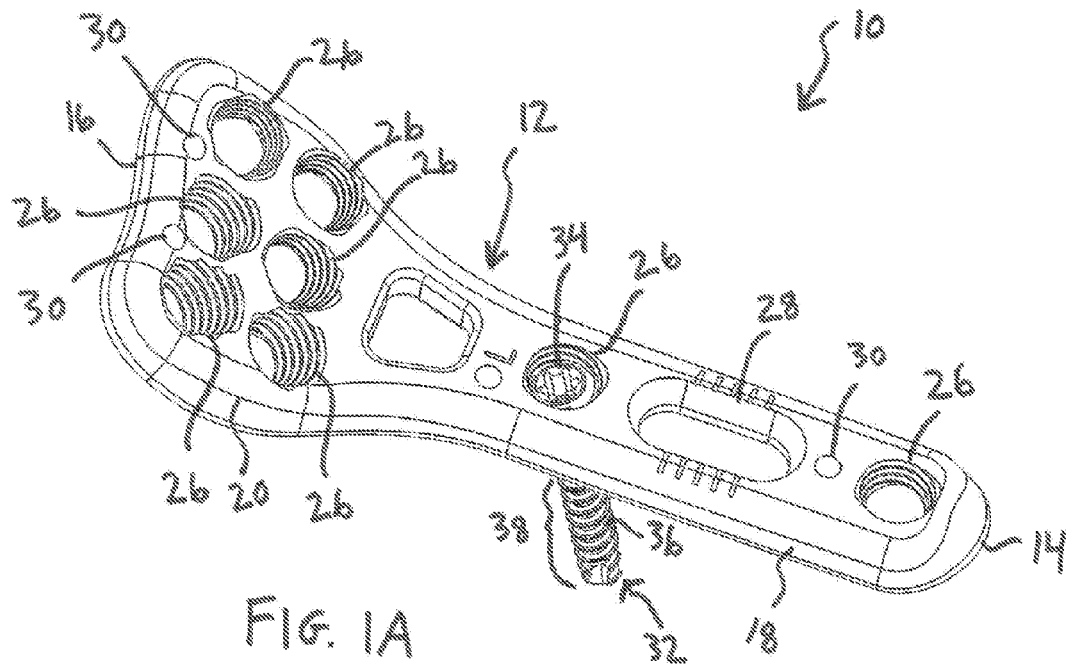
FIGS. 1A and 1B are perspective and side views, respectively, of a bone plate system in accordance with at least one example of the present disclosure.
Figure 1B:
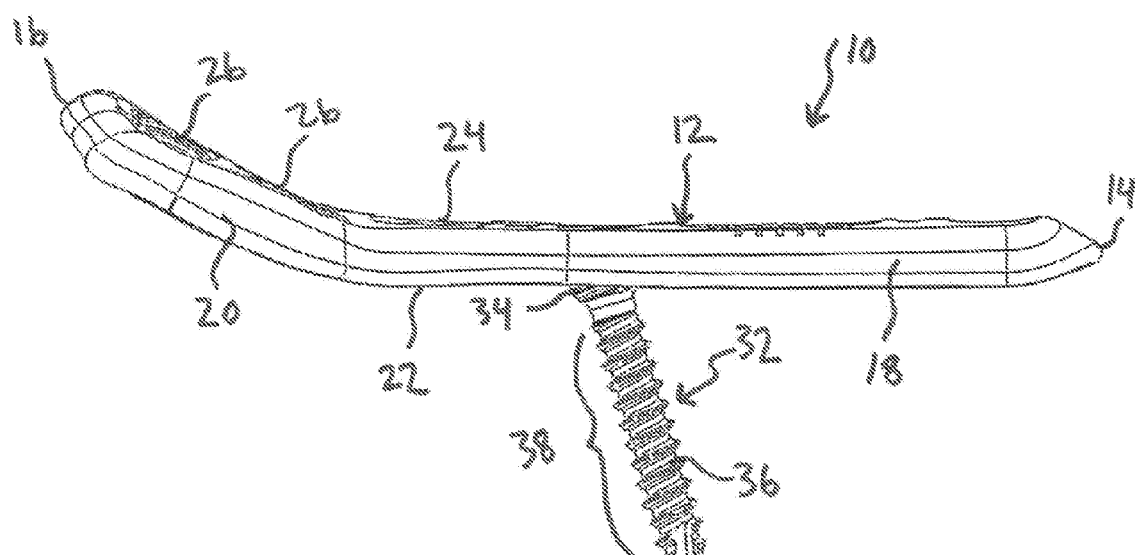

FIGS. 1A and 1B are perspective and side views, respectively, of a bone plate system 10 in accordance with at least one example of the present disclosure. As illustrated in FIG. 1, the bone plate system 10 can include a bone plate 12 having a proximal end 14, a distal end 16, a stem portion 18, and a head portion 20. With reference to FIG. 1B, the bone plate 12 can include a bone contacting first surface 22 configured for placement against one or more bones in a patient's body, and a second surface 24 generally opposing the first surface 22.

At least one of the stem portion 18 and the head portion 20 can include one or more internally threaded apertures 26 extending between the first surface 22 and the second surface 24 of the bone plate 12 and configured to receive a locking fastener (e.g., a fastener with a threaded head), as will be discussed in further detail below. FIG. 1A depicts two threaded apertures 26 in the stem portion 18 and six threaded apertures 26 in the head portion 20 merely for purposes of example and not limitation. Thus, bone plates having one or more threaded apertures are contemplated and within the scope of the present disclosure. Although not shown in FIGS. 1A and 1B, the bone plate 12 can include one or more non-threaded apertures configured to receive a non-locking fastener (e.g., a fastener with a non-threaded head). Furthermore, the threaded apertures 26 can also receive non-locking fasteners.

In various examples, the bone plate 12 can also include one or more elongated slots 28 and one or more K-wire holes 30. In an example, during initial fixation and placement of the bone plate 12, each elongated slot 28 can be configured to receive a fastener. The fastener can be loosely tightened in place on the bone to allow for longitudinal adjustment of the bone plate 12 to the final, desired position. Once the desired position has been achieved, the fastener can be further tightened within the elongated slot 28. In an example, the K-wire holes 30 can be configured for insertion of K-wires at various angles in order to temporarily fix the bone plate 12 to the underlying bone or to target bone fragments. The K-wires can be removed from the K-wire holes 30 after the bone plate 12 is secured to the bone, such as after inserting fastener into one or more of the internally threaded apertures 26.

As further illustrated in FIGS. 1A and 1B, the threaded apertures 26 can be configured to receive a locking fastener 32 (only one being shown). The locking fastener 32 can include an externally threaded head 34 configured to engage the internally threaded aperture 26. As will be discussed in further detail below, the locking fastener 32 can be inserted into the threaded aperture 26 in a plurality of different insertion angles while achieving a locking engagement between the threaded head 34 and the threaded aperture 26. The locking fastener 32 can further include an elongate shaft 36 configured for insertion within a bone underlying the plate 12. In an example, the elongate shaft 36 can include one or more external threads 38, as shown in FIGS. 1A and 1B. This type of locking fastener can be generally referred to as a "locking screw." In other examples, the elongate shaft 36 can include a substantially smooth outer surface (i.e., no external threads). This type of locking fastener can be generally referred to as a "locking peg."

Figure 2A:
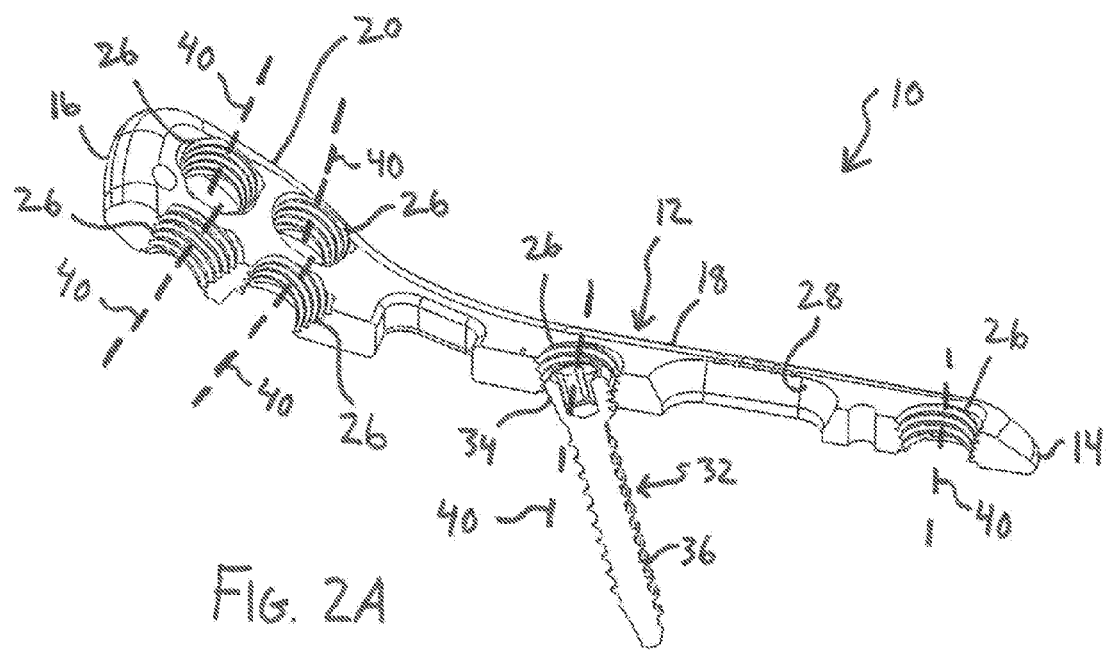
FIGS. 2A and 2B are cross-sections of the perspective and side views of FIGS. 1A and 1B, respectively, in accordance with at least one example of the present disclosure.
Figure 2B:
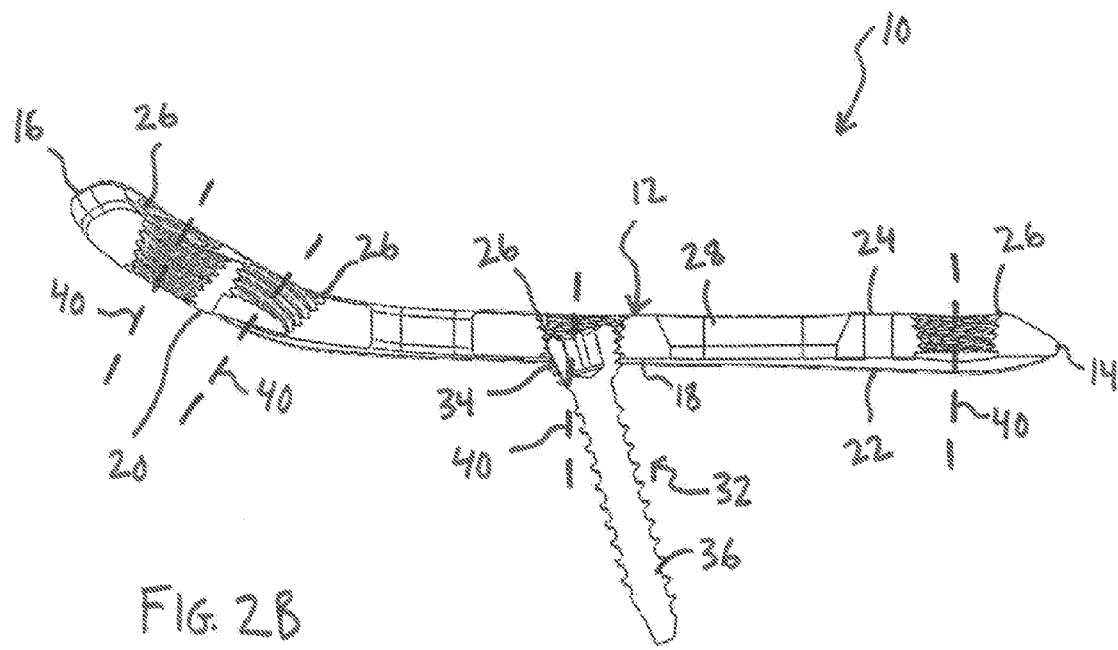

FIGS. 2A and 2B are cross-sections of the perspective and side views of FIGS. 1A and 1B, respectively, in accordance with at least one example of the present disclosure. As illustrated in FIGS. 2A and 2B, each of the threaded apertures 26 can define a longitudinal axis 40 extending through the threaded aperture 26 between the first surface 22 and the second surface 24 of the bone plate 12. The longitudinal axis 40 can represent the "centerline" of the threaded aperture 26 and is therefore dependent on the orientation in which the threaded aperture 26 is formed in the bone plate 12. In various examples, the threaded aperture 26 can be formed in the bone plate 12 such that it extends generally perpendicular to the first surface 22 and the second surface 24, or the threaded aperture 26 can be formed in the bone plate 12 such that it extends at a non perpendicular angle relative to the first surface 22 and the second surface 24. Regardless of the orientation of the threaded aperture 26, the longitudinal axis 40 defines only one of the axes along which the locking fastener 32 can be inserted. Thus, the threaded aperture 26 and the locking fastener 32 can define a "polyaxial" fastening system wherein the locking fastener 32 can be inserted into the threaded aperture 26 in a plurality of different insertion angles relative to the longitudinal axis 40 of the aperture while achieving a locking engagement between the thread head 34 and the threaded aperture 26. An example of this polyaxial locking capability is illustrated in FIGS. 2A and 2B, wherein the elongate shaft 36 of the locking fastener 32 does not extend along the longitudinal axis 40 of the corresponding threaded aperture 26, but instead forms an angle with the longitudinal axis 40 while maintaining a locking connection between the externally threaded head 34 and the internally threaded aperture 26.

Figure 3:
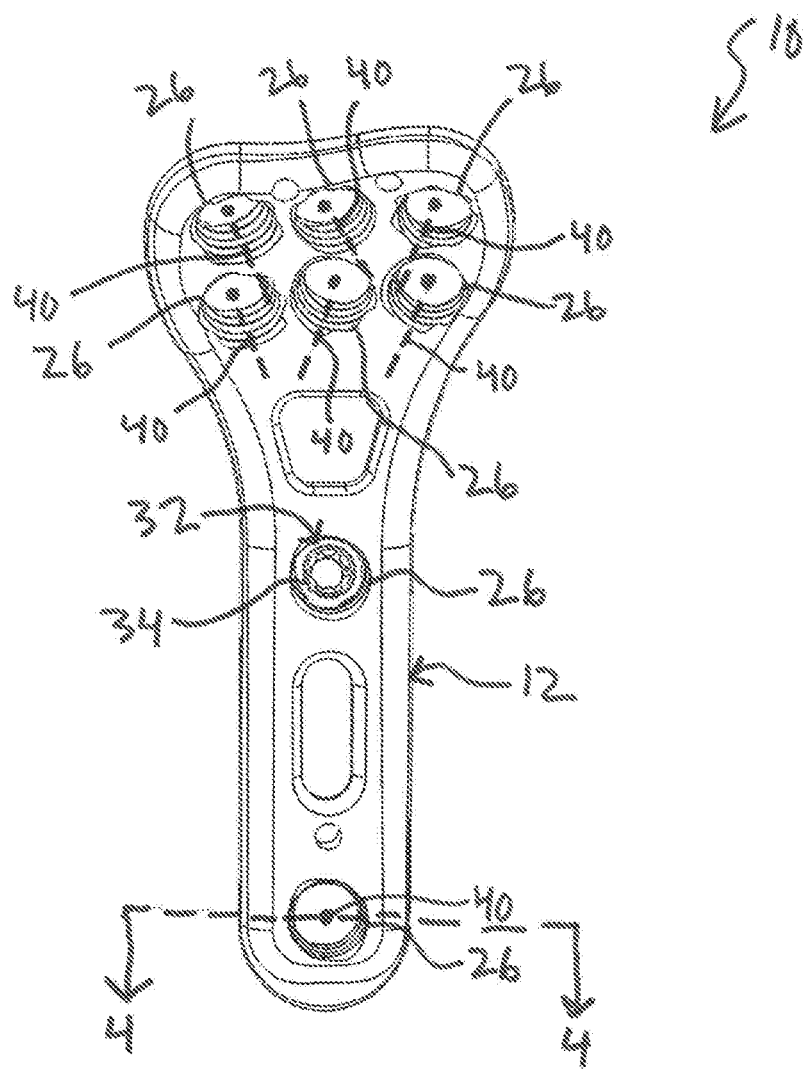
FIG. 3 is a top view of the bone plate system in accordance with at least one example of the present disclosure.

FIG. 3 is a top view of the bone plate system 10 in accordance with at least one example of the present disclosure further illustrating the longitudinal axes 40 of the threaded apertures 26 of FIGS. 2A and 2B. As shown in FIG. 3, the threaded apertures 26 can be oriented in different directions along the bone plate 12. In an example, the orientations of the threaded apertures 26 can represent common or "default" orientations that have been found to result in secure attachment of the bone plate 12 to the underlying bones and/or bone fragments. Thus, a surgeon can choose to insert the locking fastener 32 along the longitudinal axis 40 of a selected aperture 26 and achieve a locking engagement between the externally threaded head 34 of the locking fastener 32 and the internally threaded aperture 26. However, if the "default" orientation is not desirable for one or more reasons, then the surgeon can choose to utilize the polyaxial capabilities of bone plate system 10 and insert the locking fastener 32 into the threaded aperture 26 at an off-axis insertion angle. The structure of the threaded apertures 26 and the locking fasteners 32 that allows for such polyaxial locking capabilities will be further described with reference to FIGS. 4-10.

Figure 4:
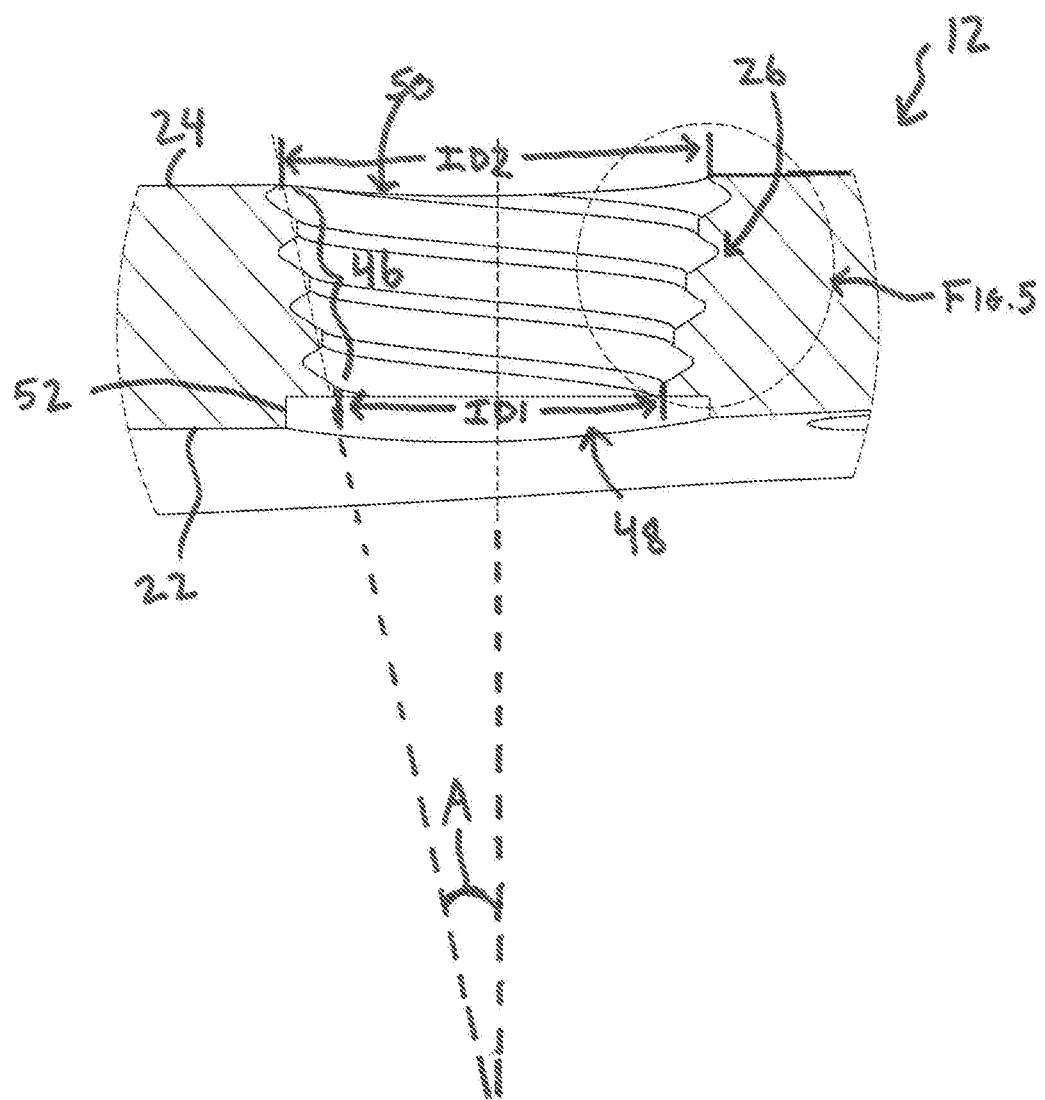
FIG. 4 is a cross-sectional view of a threaded aperture of the bone plate system in accordance with at least one example of the present disclosure.

FIG. 4 is a cross-sectional view of one of the threaded apertures 26 in the bone plate 12 taken along line 4-4 of FIG. 3. As illustrated in FIG. 4, the threaded aperture 26 can include an internally threaded surface 46 comprising one or more helical threads. The internally threaded surface 46 can include any thread pitch suitable for mating with the externally threaded head 34 of the locking fastener 32. In an example, the thread pitch can be between about 0.02 inches and about 0.06 inches, such as about 0.039 inches.

As further illustrated in FIG. 4, the threaded aperture 26 can be a tapered aperture, such as a conical tapered aperture.

The threaded aperture 26 can have a first opening 48 having a first internal diameter ID1 and a second opening 50 having a second internal diameter ID2 that is larger than the first internal diameter ID1. In an example, the first internal diameter ID1 can be about 0.130 inches and the second internal diameter ID2 can be about 0.170 inches. A taper angle A can be defined between the longitudinal axis 40 and the internally threaded surface 46 of the threaded aperture 26. Although any suitable taper angle A can be used, suitable taper angles A can be between about 5 degrees and about 25 degrees, and more particularly between about degrees and about 20 degrees, such as about 14 degrees.

With further reference to FIG. 4, the threaded aperture 26 can include a recess or counterbore in one or more of the first surface 22 and the second surface 24. For example, the bone plate 12 of FIG. 4 includes a counterbore 52 in the first surface 22. However, the counterbore 52 could alternatively be formed in the second surface 24, or a pair of counterbores 52 could be formed in the first surface 22 and the second surface 24. The one or more counterbores 52 can be configured to improve repeatability of polyaxial locking performance and allow the threaded aperture 26 to be more easily inspected after manufacture.

Figure 5:
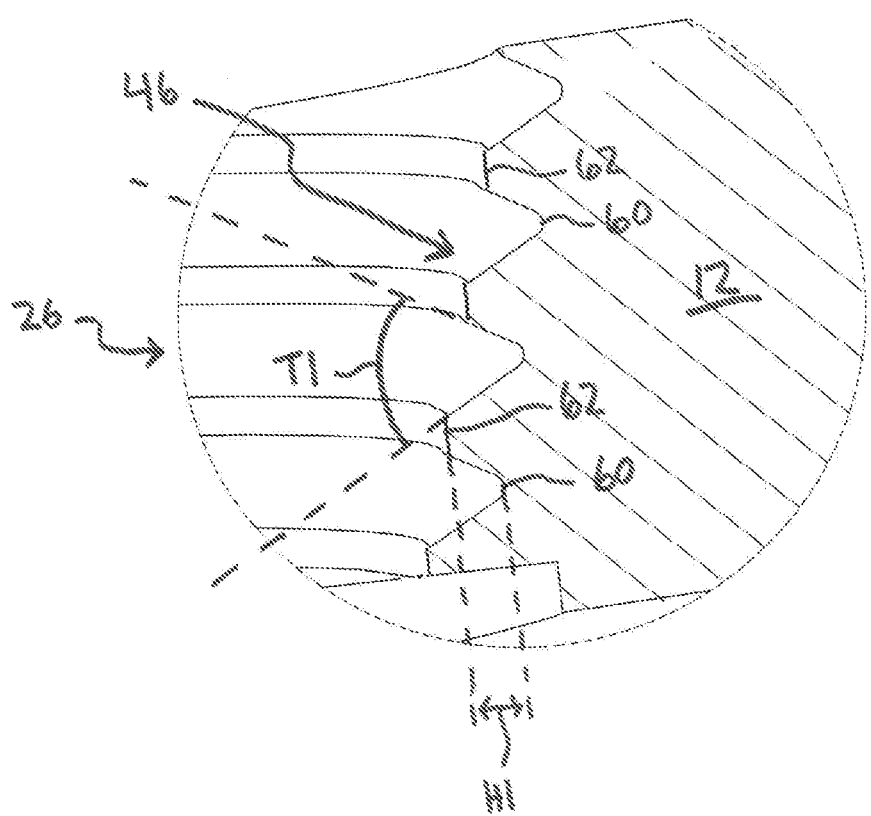
FIG. 5 is an enlarged cross-sectional view of a portion of the threaded aperture of FIG. 4.

FIG. 5 is an enlarged cross-sectional view of a portion of the threaded aperture 26 of FIG. 4. In various examples within the scope of the present disclosure, the internally threaded surface 46 of the threaded aperture 26 can define a single lead or multiple leads. The threaded aperture 26 of FIGS. 4 and 5 illustrates a double lead with start points spaced apart by about 180 degrees.

The internally threaded surface 46 can include V-shaped threads defining a series of roots 60 and crests 62 and having an internal thread angle T1. The thread angle T1 can be selected such that it is consistent with commercially available tooling, such as 60 degrees (UN threads) or 29 degrees (ACME threads). However, various other non-standard thread angles can be used. In the present example of the bone plate 12, the internal thread angle T1 is about 60 degrees. A thread height H1 of the threads of the internally threaded surface 46 can be defined between one of the roots 60 and an adjacent one of the crests 62. As illustrated in FIG. 5, the roots 60 and/or the crests 62 can be truncated to avoid the formation of a "sharp" V-shape. A perfectly sharp 60 degree V-thread generally includes a thread height equal to about 0.866 of the pitch. However, with truncated threads, the thread height decreases. In an example, the thread height H1 can be between about 0.008 inches and about 0.015 inches, such as about 0.0118 inches.

Figure 6:
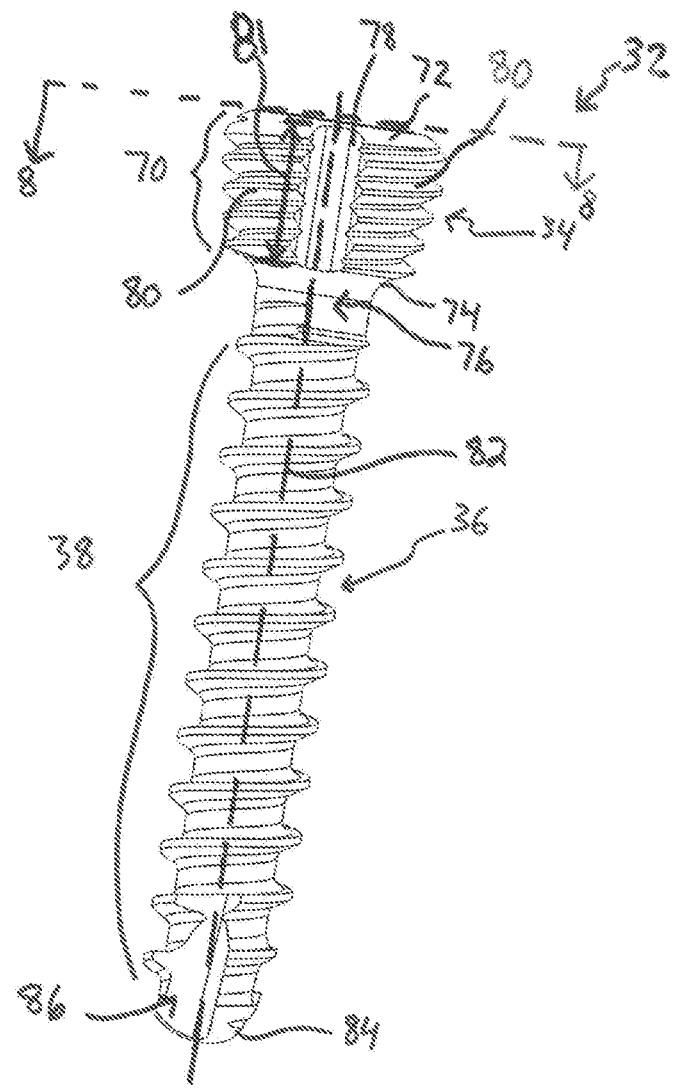
FIG. 6 is a side view of a locking fastener in accordance with at least one example of the present disclosure.

FIG. 6 is a side view of the locking fastener 32 in accordance with at least one example of the present disclosure. As illustrated in FIG. 6, the threaded head 34 of the locking fastener 32 can include an externally threaded surface 70 comprising one or more helical threads. The externally threaded surface 70 can include any thread pitch suitable for mating with the internally threaded surface 46 of the threaded aperture 26. In an example, the thread pitch may be between about 0.02 inches and about 0.06 inches, such as about 0.039 inches. The thread pitch of the externally threaded surface 70 of the threaded head 34 can be substantially identical to the thread pitch of the internally threaded surface 46 of the threaded aperture 26. However, the thread pitch between the threaded head 34 of the locking fastener 32 and the threaded aperture 26 of the bone plate 12 can be varied such that there is a mismatch between thread pitches. In an example, a mismatch between thread pitches can increase the locking strength by increasing the contact area on the flanks of the threads in the externally threaded surface 70.

In various examples within the scope of the present disclosure, the externally threaded surface 70 of the threaded head 34 can define a single lead or multiple leads. Similar to the threaded aperture 26 of FIGS. 4 and 5, the threaded head 34 of FIG. 6 illustrates a double lead with start points spaced apart by about 180 degrees.

The threaded head 34 can include a proximal end 72 and a distal end 74. A non-threaded transition region 76 can be provided between the threaded head 34 and the elongate shaft 36 adjacent to the distal end 74 of the threaded head 34. As further illustrated in FIG. 6, the threaded head 34 can include one or more recesses 78 circumferentially spaced around the threaded head 34 and defining a plurality of threaded tabs 80. In an example, the one or more recesses 78 can be formed by creating tangential cuts in the externally threaded surface 70 of the threaded head 34. The tangential cuts can have a depth sufficient to completely remove the threads in the area of the recess 78 such that a substantially smooth recessed surface is created. Alternatively, the recess 78 can be formed to a depth that retains the threads in the area of the recess 78, albeit at a reduced height (between a root and a crest of the thread).

Each of the one or more recesses 78 can extend in a direction 81 at least partially between the proximal end 72 and the distal end 74 of the threaded head 34 that can be substantially parallel to a longitudinal axis 82 of the locking fastener 32. The longitudinal axis 82 can extend through a center of the threaded head 34 and a center of the elongate shaft 36. Thus, the longitudinal axis 82 can alternatively be defined as the longitudinal axis of the threaded head 34 or the longitudinal axis of the elongate shaft 36. In other examples, at least one of the one or more recesses 78 can extend in a direction 81 between the proximal end 72 and the distal end 74 of the threaded head 34 that forms a non-zero angle with, and is therefore not parallel to, the longitudinal axis 82 of the locking fastener 32. Thus, the one or more recesses 78 can extend in a direction that forms a non-perpendicular angle with a plane defined along the proximal end 72 of the threaded head 34 and a plane defined along the distal end 74 of the threaded head 34 (i.e., a "slanted" recess).

With further reference to FIG. 6, a distal end 84 of the elongate shaft 36 can include a self-tapping tip 86 comprising one or more flutes. The self-tapping tip 86 can provide the locking fastener 32 with the ability to advance in a longitudinal direction when being turned, while at the same time creating its own thread in the bone. In other examples, the elongate shaft 36 does not include a self-tapping tip 86, and the bone can be pre-chilled prior to insertion of the locking fastener 32.

The one or more external threads 38 on the elongate shaft 36 can have the same pitch and the same lead as the externally threaded surface 70 of the threaded head 34. In other examples, the one or more external threads 38 can have a pitch and/or a lead that is different than the externally threaded surface 70, such as a double lead on the threaded head 34 and a single lead on the elongate shaft 36.

Figure 7:
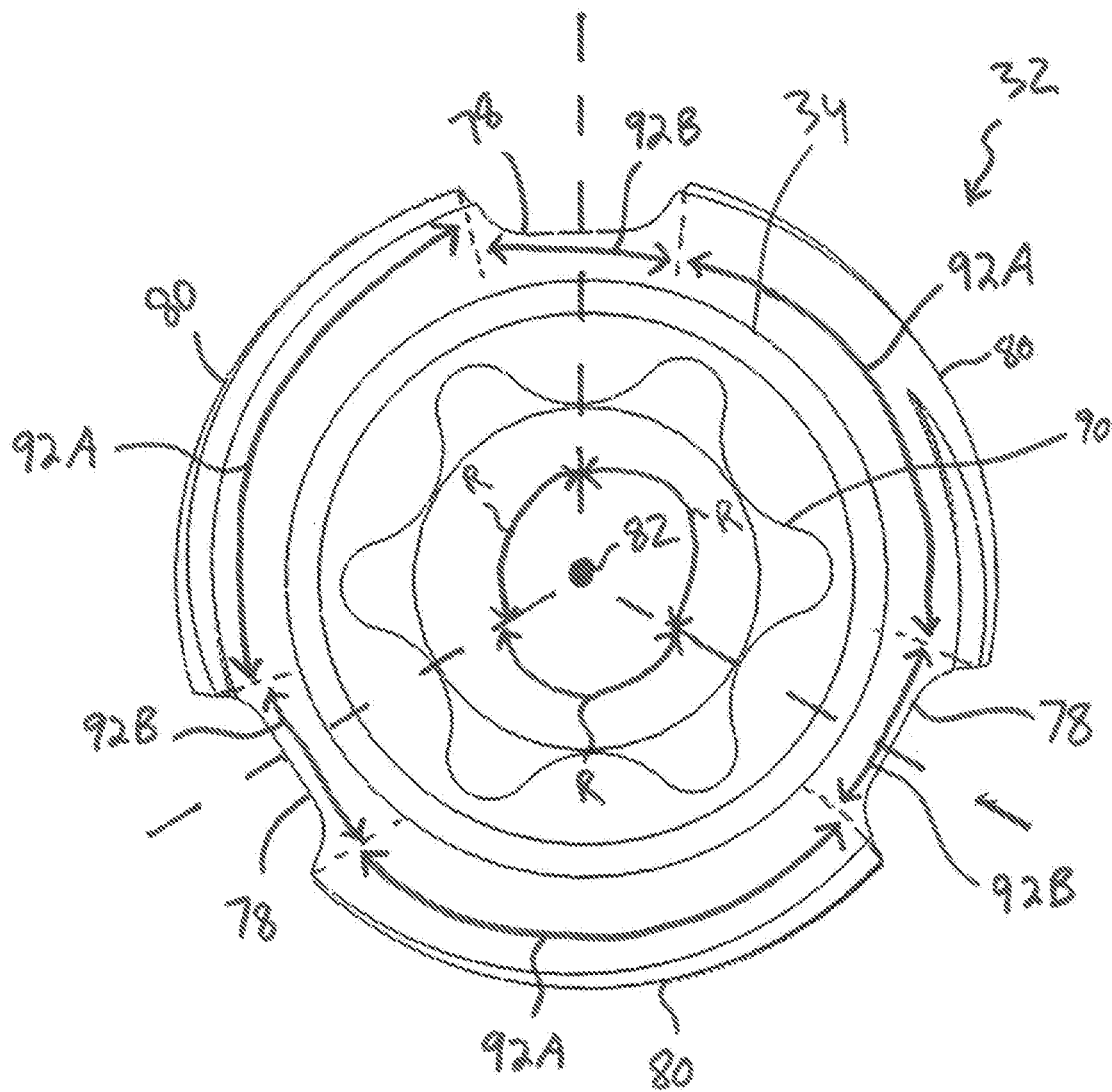
FIG. 7 is a proximal end view of the locking fastener in accordance with at least one example of the present disclosure.

FIG. 7 is a proximal end view of the locking fastener 32 of FIG. 6 in accordance with at least one example of the present disclosure. As illustrated in FIG. 7, the threaded head 34 of the locking fastener 32 can include a drive interface 90, such as a female drive interface configured to mate with a male drive interface on a driver device. In an example, as shown in FIG. 7, the drive interface 90 can be a hexalobe drive interface. However, any suitable drive interface 90 can be used including, but not limited to, a hex drive interface, a double hex drive interface, a pentagon drive interface, a square drive interface, a slotted drive interface, a cross-recess drive interface, a Phillips drive interface, a Frearson drive interface, a Mortorq drive interface, a Pozidriv drive interface, a Supadriv drive interface, a Phillips/square drive interface, a pentalobe drive interface, a polydrive interface, or a spline drive interface.

As discussed above, the threaded head 34 of the locking fastener 32 can include one or more recesses 78. In the example illustrated in FIG. 7, the threaded head 34 includes three recesses 78 spaced circumferentially around a perimeter of the threaded head 34 by an angle R of about 120 degrees. In various examples, a larger or smaller number of recesses 78 can be included, such as between 2 recesses and 5 recesses. The angular spacing can be, but is not necessarily, equal between adjacent recesses 78. Thus, in an example, the angle R defined between adjacent recesses 78 can be determined from the equation (R=360 degrees/X), where X is the total number of recesses in the threaded head 34. However, the recesses 78 can be non-uniformly spaced such that at least one of the angles R has a value different than at least one of the other angles R.

As illustrated in FIG. 7, a circumference of the threaded head 34 can be divided into a plurality of threaded circumference portions 92A and a plurality of non-threaded circumference portions 92B (or circumference portions having a reduced thread height as discussed above). Particularly, the non-threaded circumference portions 92B can be defined by the portions of the externally threaded surface 70 that have been removed by the recesses 78, and the threaded circumference portions 92A can be defined by the remaining portions of the externally threaded surface 70. Thus, the threaded circumference portions 92A and the non-threaded circumference portions 92B can be viewed in terms of the circumferential widths of these portions around the threaded head 34 (in a plane perpendicular to the longitudinal axis 82 of the locking fastener 32), or in terms of the circumferential surface areas of these portions determined by factoring in the circumferential widths and the lengths of the portions between the proximal end 72 of the threaded head 34 and the distal end 74 of the threaded head 34 (see FIG. 6). Regardless of whether the threaded circumference portions 92A and the non-threaded circumference portions 92B are viewed as circumferential widths or circumferential surface areas, in an example, the removed "circumference" of the recesses 78 can be less than the remaining "circumference" of the tabs 80 as depicted in FIGS. 6 and 7. In other examples, however, the removed "circumference" of the recesses 78 can be equal to or greater than the remaining "circumference" of the tabs 80.

Figure 8:
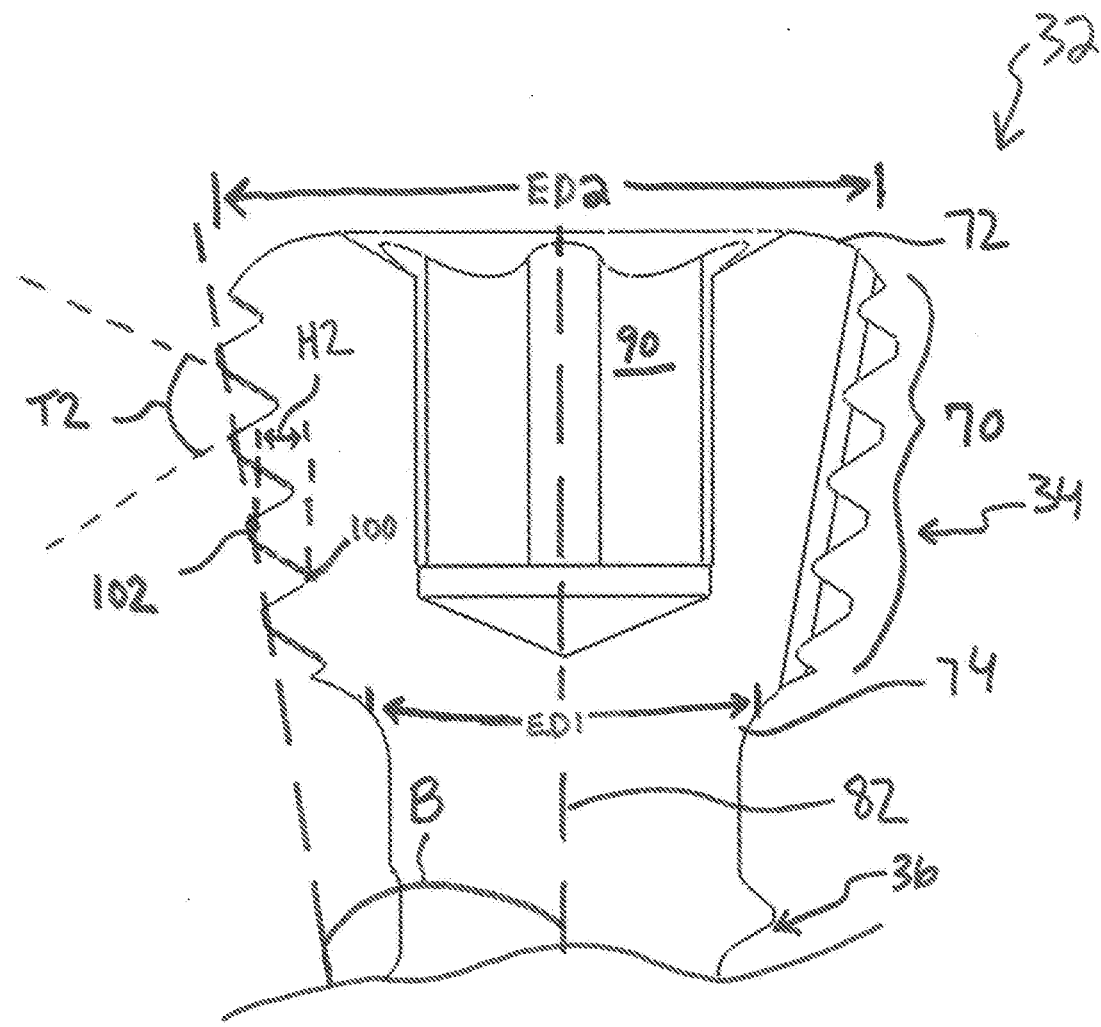
FIG. 8 is a cross-sectional view of a portion of the locking fastener in accordance with at least one example of the present disclosure.

FIG. 8 is a cross-sectional view of a portion of the locking fastener 32 taken along line 8-8 of FIG. 6. As illustrated in FIG. 8, the threaded head 34 can be a tapered head, such as a conical tapered head. The threaded head 34 can have a first external diameter ED1 at the distal end 74 and a second external diameter ED2 at the proximal end 72 that is larger than the first external diameter ED1. In an example, the first external diameter ED1 can be about 0.132 inches and the second external diameter ED2 can be about 0.1.57 inches. A taper angle B can be defined between the longitudinal axis 82 of the locking fastener 32 and the externally threaded surface 70 of the threaded head 34. Although any suitable taper angle B can be used, suitable taper angles A can be between about 2 degrees and about 20 degrees, and more particularly between about 5 degrees and about 15 degrees, such as about 10 degrees.

As previously described, the threaded aperture 26 of the bone plate 12 and the locking fastener 32 can define a "polyaxial." fastening system wherein the locking fastener 32 can be inserted into the threaded aperture 26 in a plurality of different insertion angles relative to the longitudinal axis 40 of the aperture while achieving a locking engagement between the threaded head 34 and the threaded aperture 26. The ability of the locking fastener 32 to be received within the threaded aperture 26 at a plurality of different insertion angles can result from, at least in part, the "mismatch" in taper angles between the internally threaded aperture 26 and the externally threaded head 34 of the locking fastener 32. More particularly, the taper angle B of the threaded head 34 can be configured such that it is smaller than the taper angle A of the threaded aperture 26, thereby allowing insertion of the locking fastener 32 in a range of insertion angles. Furthermore, the larger taper angle A in the bone plate 12 can create more congruence between the internally threaded aperture 26 and the externally threaded head 34 of the locking fastener 32 as the insertion angles of the locking fastener 32 become larger. This can be important because the locking strength is typically reduced as the insertion angle of a locking fastener is increased.

The particular range of insertion angles can depend on, for example, the magnitude of the mismatch in taper angles between the threaded aperture 26 and the threaded head 34. In various examples, the range of insertion angles (relative to the longitudinal axis 40 of the threaded aperture 26) can be between 0 degrees and about 30 degrees, such as between 0 degrees and about 15 degrees.

The externally threaded surface 70 can include V-shaped threads defining a series of roots 100 and crests 102 and having an internal thread angle T2. Similar to the thread angle T1 of the threaded aperture 26, the thread angle T2 can be selected such that it is consistent with commercially available tooling, such as 60 degrees (UN threads) or 29 degrees (ACME threads), although various other non-standard thread angles can be used. In the present example of the locking fastener 32, the thread angle T2 of the threaded head 34 can be substantially equal to the thread angle T1 of the threaded aperture 26, or about 60 degrees. A thread height H2 of the threads of the externally threaded surface 70 can be defined between one of the roots 100 and an adjacent one of the crests 102. As illustrated in FIG. 8, the roots 100 and/or the crests 102 can once again be truncated to avoid the formation of a "sharp" V-shape. In an example, the thread height H2 can be between about 0.009 inches and about 0.020 inches, such as about 0.0137 inches.

Figure 9:
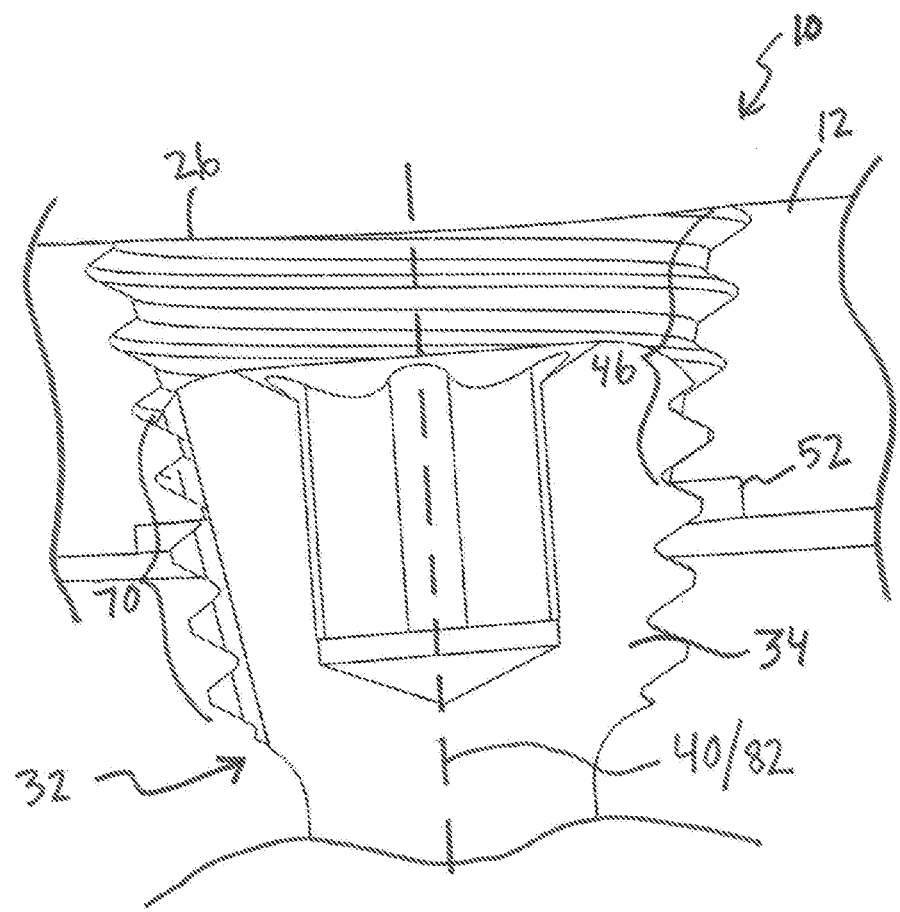
FIG. 9 depicts the locking fastener at an on-axis insertion angle of 0 degrees in accordance with at least one example of the present disclosure.
Figure 10:
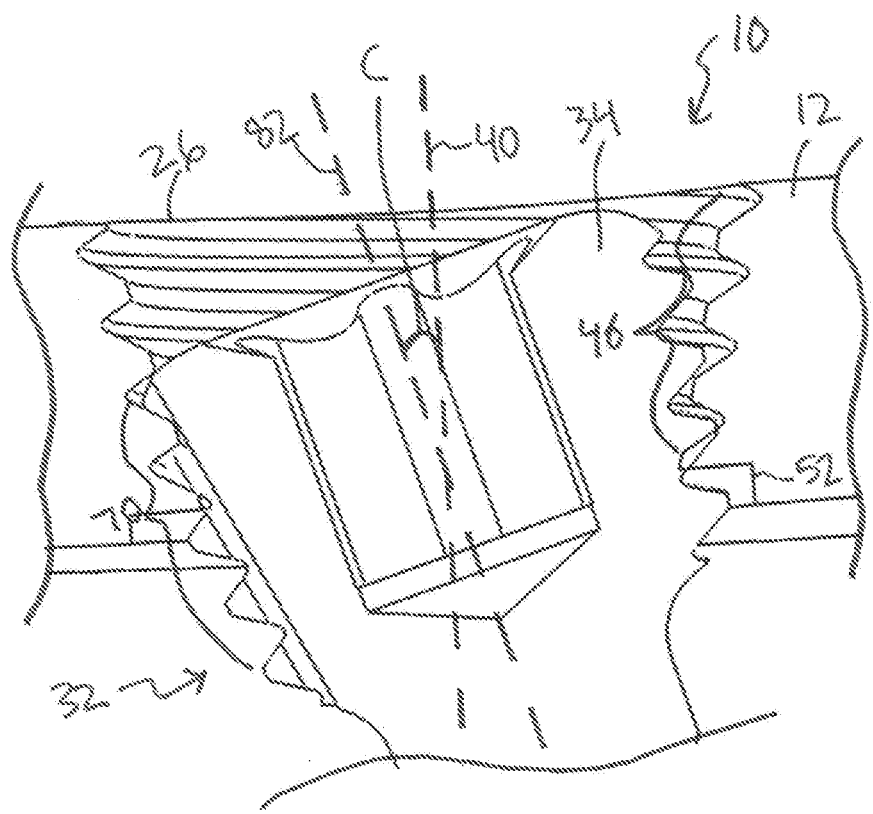
FIG. 10 depicts the locking fastener inserted at an off-axis, non-zero insertion angle in accordance with at least one example of the present disclosure.

FIGS. 9 and 10 are cross-sectional views of a portion of the bone plate system 10 illustrating the polyaxial locking capability of the locking fastener 32 and the threaded aperture 26 of the bone plate 12. In particular, FIG. 9 depicts the locking fastener 32 at an insertion angle of 0 degrees, wherein the longitudinal axis 82 of the locking fastener 32 is aligned with the longitudinal axis 40 of the threaded aperture 26. In the straight on-axis insertion shown in FIG. 9, at least a portion of the externally threaded surface 70 of the threaded head 34 can engage at least a portion of the internally threaded surface 46 of the threaded aperture 26 such that the threads are aligned an no cross-threading occurs. During on-axis insertion of the locking fastener 32, there can be continuous contact between the externally threaded surface 70 of the locking fastener 32 and the internally threaded surface 46 of the threaded aperture 26.

The counterbore 52 in the first surface 22 of the bone plate 12 can be configured to receive a thread portion of the externally threaded surface 70 after insertion through the threaded aperture 26.

FIG. 10 depicts the locking fastener 32 inserted at an off-axis, non-zero insertion angle relative to the longitudinal axis 40 of the threaded aperture 26. In particular, the longitudinal axis 82 of the locking fastener 32 can define an insertion angle C with the longitudinal axis 40 of the threaded aperture 26. As discussed above, the particular range of insertion angles C can depend on factors such as, for example, the magnitude of the mismatch in taper angles between the threaded aperture 26 and the threaded head 34. In various examples, the range of insertion angles C can be between 0 degrees and about 30 degrees, such as between 0 degrees and about 15 degrees as depicted in FIGS. 9 and 10.

When the locking fastener 32 is inserted into the threaded aperture 26 at an off-axis, non-zero insertion angle C, the threaded tabs 80 defined by the recesses 78 in the threaded head 34 (see FIG. 6) can deform to seat into the threaded surface 46 of the aperture 26. This deformation of the threaded tabs 80 can couple with hoop stresses caused by the off-axis insertion to create a lock between the threaded head 34 and the threaded aperture 26. In view of the foregoing, by providing a larger taper angle in the threaded aperture 26 of the bone plate 12 than on the threaded head 34 of the locking fastener 32, and by further providing a plurality of threaded tabs 80 on the threaded head 34, the locking fastener 32 can be inserted into the threaded aperture at a plurality of different off-axis insertion angles while maintaining congruence between the internally threaded surface 46 of the threaded aperture 26 and the externally threaded surface 70 of the threaded head 34, even at large off-axis angles of 15 degrees or more.

Unlike the on-axis insertion illustrated in FIG. 9, when the locking fastener 32 is inserted off-axis as illustrated in FIG. 10, a portion of the externally threaded surface 70 of the threaded head 34 that is disposed within the threaded aperture 26 may not actually engage the internally threaded surface 46 of the aperture 26. Even though there may not be continuous contact between the externally threaded surface 70 of the locking fastener 32 and the internally threaded surface 46 of the threaded aperture 26, the off-axis threaded engagement can still maintain a locked coupling engagement between the components.

The bone plate 12 and the locking fastener 32 can be formed from any suitable medical-grade material. Exemplary materials can include, but are not limited to, stainless steel, titanium, and cobalt based alloys. The bone plate 12 and the locking fastener 32 can be formed from the same material or at least partially from different materials. One or both of the locking fastener 32 and the bone plate 12 can be anodized or hard-coated to reduce insertion torque of the locking fastener 32 into the threaded aperture 26. An example of a suitable coating can be Titanium Nitride (TiN).

The materials and coatings for the bone plate 12 and the locking fastener 32 can be mismatched to facilitate selective deformation of one component relative to the other. In an example, the threaded head 34 of the locking fastener 32 can be formed from a material and/or include a coating that is softer than the bone plate 12 to allow deformation of the threaded head 34 during insertion. Such a design can allow a first locking fastener to be removed and replaced with a second locking fastener without any damage to the threaded aperture in the bone plate.

The above Detailed Description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A bone plate system, comprising:
   a bone plate including a first surface and a second surface, the bone plate including at least one threaded aperture, the threaded aperture being conically tapered between the first surface and the second surface at a first taper angle; and
   at least one fastener including an elongate shaft and a threaded head, the threaded head being conically tapered between a proximal end of the threaded head and a distal end of the threaded head at a second taper angle different from the first taper angle, wherein a plurality of circumferentially spaced recesses are formed in the threaded head and define a plurality of threaded tabs;

wherein the first taper angle is formed between a longitudinal axis of the threaded aperture and an entirely threaded surface of the threaded aperture, the entirely threaded surface being conically tapered; and wherein the at least one fastener is configured for insertion within the at least one threaded aperture at a plurality of different insertion angles while achieving a locking engagement between the threaded head and the threaded aperture.

2. The bone plate system of claim 1, wherein the second taper angle is formed between a longitudinal axis of the threaded head and an externally threaded surface of the threaded head, the first taper angle being greater than the second taper angle.

3. The bone plate system of claim 2, wherein the first taper angle is between 10 degrees and 20 degrees, and wherein the second taper angle is between 5 degrees and 15 degrees.

4. The bone plate system of claim 2, wherein the plurality of recesses extend from the proximal end to the distal end of the threaded head in a direction that is substantially parallel to the longitudinal axis of the threaded head.

5. The bone plate system of claim 2, wherein the threaded surface of the threaded aperture includes double lead threads.

6. The bone plate system of claim 1, wherein the threaded aperture includes internal threads defining a first pitch, and wherein the threaded head includes external threads defining a second pitch.

7. The bone plate system of claim 6, wherein the first pitch and the second pitch are the same.

8. The bone plate system of claim 6, wherein the first pitch and the second pitch are different.

9. The bone plate system of claim 1, comprising three or more recesses formed in the threaded head.

10. The bone plate system of claim 1, wherein a circumference of the threaded head includes a threaded circumference portion defined by the threaded tabs and a non-threaded circumference portion defined by the recesses, wherein the threaded circumference portion is greater than the non-threaded circumference portion.

11. The bone plate system of claim 1, wherein the threaded head is at least partially formed from a first material that is softer than a second material of the bone plate such that the threaded head can deform during insertion within the threaded aperture of the bone plate.

12. A bone plate system, comprising:
a bone plate including a bone facing surface, an opposing outer surface, and at least one linearly tapered aperture extending through the bone plate and having a longitudinal axis and a threaded internal surface, the linearly tapered aperture defining a first taper angle between the longitudinal axis of the linearly tapered aperture and the threaded internal surface, the outer surface further including a first counterbore centered about the longitudinal axis of the linearly tapered aperture, and the bone facing surface further including a second counterbore centered about the longitudinal axis of the linearly tapered aperture, the threaded internal surface being continuously linearly tapered from the first counterbore to the second counterbore; and
at least one fastener including an elongate shaft and a linearly tapered head having a threaded external surface and a longitudinal axis, the linearly tapered head defining a second taper angle between the longitudinal axis of the linearly tapered head and the threaded external surface, wherein a plurality of circumferentially spaced recesses are formed in the linearly tapered head and define interruptions in the threaded external surface of the linearly tapered head;
wherein the first taper angle of the linearly tapered aperture is greater than the second taper angle of the linearly tapered head such that the at least one fastener can be inserted within the at least one linearly tapered aperture at a plurality of different insertion angles.

13. The bone plate system of claim 12, wherein the first taper angle is between 10 degrees and 20 degrees, and wherein the second taper angle is between 5 degrees and 15 degrees.

14. The bone plate system of claim 12, wherein the interruptions in the threaded external surface of the linearly tapered head define a plurality of threaded tabs on the linearly tapered head.

15. The bone plate system of claim 14, wherein a circumferential surface area defined by the threaded tabs is greater than a circumferential surface area defined by the recesses in the linearly tapered head.

16. The bone plate system of claim 12, wherein the threaded internal surface of the linearly tapered aperture includes threads defining a first pitch and the threaded external surface of the linearly tapered head includes threads defining a second pitch, and wherein the first pitch and the second pitch are the same.

17. The bone plate system of claim 12, wherein the threaded internal surface of the linearly tapered aperture includes threads defining a first pitch and the threaded external surface of the linearly tapered head includes threads defining a second pitch, and wherein the first pitch and the second pitch are different.

18. A bone plate system, comprising:
a bone plate including a first surface and a second surface, the bone plate including at least one threaded aperture, the threaded aperture being conically tapered between the first surface and the second surface at a first taper angle; and
at least one fastener including an elongate shaft and a threaded head, the threaded head being conically tapered between a proximal end of the threaded head and a distal end of the threaded head at a second taper angle different from the first taper angle, wherein a plurality of circumferentially spaced recesses are formed in the threaded head and define a plurality of threaded tabs;
wherein the first taper angle is between 10 degrees and 20 degrees, and wherein the second taper angle is between 5 degrees and 15 degrees; and
wherein the at least one fastener is configured for insertion within the at least one threaded aperture at a plurality of different insertion angles while achieving a locking engagement between the threaded head and the threaded aperture.

19. The bone plate system of claim 18, wherein the threaded aperture includes double lead threads.

20. The bone plate system of claim 18, wherein the threaded head is at least partially formed from a first material that is softer than a second material of the bone plate such that the threaded head can deform during insertion within the threaded aperture of the bone plate.

* * * * *